(12) United States Patent
Mosnier et al.

(10) Patent No.: US 9,782,228 B2
(45) Date of Patent: *Oct. 10, 2017

(54) METHODS, SYSTEMS, AND DEVICES FOR DESIGNING AND MANUFACTURING A ROD TO SUPPORT A PATIENT'S VERTEBRAL COLUMN

(71) Applicant: Medicrea International, Rillieux-la-Pape (FR)

(72) Inventors: Thomas Mosnier, Anthon (FR); David Ryan, Collonges Au Mont d'Or (FR)

(73) Assignee: Medicrea International, Rillieux-la-Pape (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/469,302

(22) Filed: Mar. 24, 2017

(65) Prior Publication Data

US 2017/0245937 A1    Aug. 31, 2017

Related U.S. Application Data

(63) Continuation of application No. 15/024,150, filed as application No. PCT/IB2014/065150 on Oct. 8, 2014, now Pat. No. 9,693,831.

(30) Foreign Application Priority Data

Oct. 18, 2013  (FR) ...................................... 13 60208

(51) Int. Cl.
*G06T 7/00*    (2017.01)
*A61B 34/10*   (2016.01)
(Continued)

(52) U.S. Cl.
CPC .......... *A61B 34/10* (2016.02); *A61B 17/7011* (2013.01); *A61B 17/8863* (2013.01);
(Continued)

(58) Field of Classification Search
None
See application file for complete search history.

(56) References Cited

U.S. PATENT DOCUMENTS

2009/0204159 A1*  8/2009  Justis .................. A61B 17/708
                                                606/323
2009/0254326 A1* 10/2009  Isaacs ............... A61B 17/7011
                                                703/11
2015/0127055 A1*  5/2015  Dvorak ............. A61B 17/7038
                                                606/279

* cited by examiner

*Primary Examiner* — Delomia L Gilliard
(74) *Attorney, Agent, or Firm* — Knobbe Martens Olson & Bear, LLP

(57) ABSTRACT

According to the invention, the process includes the steps of: a) taking a sagittal preoperative x-ray of the vertebral column of the patient to be treated, extending from the cervical vertebrae to the femoral heads; b) on that x-ray, identifying points on S1, S2, T12 et C7; c) depicting, on the said x-ray, curved segments beginning at the center of the plate of S1 et going to the center of the plate of C7; e) identifying, on that x-ray, the correction(s) to be made to the vertebral column, including the identification of posterior osteotomies to make; f) pivoting portions of said x-ray relative to other portions of that x-ray, according to osteotomies to be made; g) performing, on said x-ray, a displacement of the sagittal curvature segment extending over the vertebral segment to be corrected; h) from a straight vertebral rod (TV), producing the curvature of that rod according to the shape of said sagittal curvature segment in said displacement position.

15 Claims, 5 Drawing Sheets

(51) Int. Cl.
*A61B 17/70* (2006.01)
*A61B 17/88* (2006.01)
A61B 17/00 (2006.01)
A61B 17/56 (2006.01)

(52) U.S. Cl.
CPC .. *G06T 7/0012* (2013.01); *A61B 2017/00526* (2013.01); *A61B 2017/568* (2013.01); *A61B 2034/108* (2016.02); *G06T 2207/30052* (2013.01)

METHODS, SYSTEMS, AND DEVICES FOR DESIGNING AND MANUFACTURING A ROD TO SUPPORT A PATIENT'S VERTEBRAL COLUMN

CROSS-REFERENCE TO RELATED APPLICATIONS

This application is a continuation of U.S. patent application Ser. No. 15/024,150, filed on Mar. 23, 2016, and titled METHOD MAKING IT POSSIBLE TO PRODUCE THE IDEAL CURVATURE OF A ROD OF VERTEBRAL OSTEOSYNTHESIS MATERIAL DESIGNED TO SUPPORT A PATIENT VERTEBRAL COLUMN, which is a U.S. national stage entry of PCT Application No. PCT/IB2014/065150, filed Oct. 8, 2014, and titled METHOD MAKING IT POSSIBLE TO ACHIEVE THE IDEAL CURVATURE OF A ROD FOR VERTEBRAL OSTEOSYNTHESIS EQUIPMENT DESIGNED TO SUPPORT A PATIENT'S VERTEBRAL COLUMN, which claims priority to and the benefit of French Patent Application No. 1360208, filed Oct. 18, 2013, and titled PROCEDE PERMETTANT DE REALISER LA COURBURE IDEALE D'UNE TIGE D'UN MATERIEL D'OSTEOSYNTHESE VERTEBRALE DESTINEE A ETAYER LA COLONNE VERTEBRALE D'UN PATIENT. The entire contents of the above-identified patent applications are incorporated by reference herein and made a part of this specification. Any and all priority claims identified in the Application Data Sheet, or any correction thereto, are hereby incorporated by references under 37 CFR 1.57.

FIELD OF THE INVENTION

The present invention relates to a method making it possible to produce the ideal curvature of a rod for vertebral osteosynthesis equipment designed to correct a patient's vertebral column.

BACKGROUND OF THE INVENTION

It is known to analyze a patient's vertebral column in reference to so called "pelvic" parameters that are documented in the scientific literature. The appended FIG. 1 very diagrammatically shows the base of a vertebral column, i.e., a part of the lumbar vertebrae L and the sacrum S, as well as the femoral heads TF; said pelvic criteria are:

the SS (sacral slope) criterion, which is the incline angle of the plate of S1 (first vertebra of the sacrum), relative to the horizontal;

the PV (pelvic version) criterion, which is the angle formed by the straight segment connecting the center of the femoral heads TF and the center of the plate of S1 with the vertical;

the PI (pelvic incidence) criterion, which is the angle formed by the straight segment connecting the center of the femoral heads TF and the center of the plate of S1 with the perpendicular to the plate of S1.

It is accepted that an individual will adopt a natural vertebral column posture, called "economic", avoiding pain and other pathologies, if his pelvic parameters in particular are in agreement with his back morphotype. If this is not the case, surgical treatment may be considered in order to reestablish proper posture of the vertebral column, in which that agreement exists.

It is well known to perform this type of recovery using rigid vertebral rods, in particular metal, fastened to the vertebrae using pedicle screws, which must be curved suitably based on the correction to be done. The publication of patent application No. WO 98/55038 illustrates an equipment of this type.

It has been shown that imparting the appropriate curvature to a straight rod may be very difficult for a surgeon, the curvature being more or less pronounced in any given location of the rod. Currently, such a curvature is done at the surgeon's discretion and a call greatly on the latter's experience and dexterity. The trial and error necessary to obtain an appropriate curvature have the significant drawback of extending the operation time, which is not desirable for the patient, and the risk of implanting a rod with a non-ideal curvature cannot be ruled out.

OBJECTS OF THE INVENTION

The present invention aims to resolve this essential drawback.

Patent application publications Nos. WO 2004/017836 A2, US 2009/254326 A1 and WO 2008/079546 A2 describe methods not making it possible to achieve the same in a satisfactory manner.

SUMMARY OF THE INVENTION

To achieve that aim, the method according to the invention comprises the following steps:

a) taking a sagittal preoperative x-ray of the vertebral column of the patient to be treated, extending from the cervical vertebrae to the femoral heads;

b) on that x-ray, identifying:

the points and straight segments making it possible to calculate the so-called "pelvic" parameters, i.e., the sacral slope, the pelvic version and the pelvic incidence, the center of the plate of the first vertebra of the sacrum, called S1;

the center of the second vertebra of the sacrum, called S2;

the center of the lower plate of a reference dorsal vertebra, in particular the twelfth dorsal vertebra, called T12;

the center of the lower plate of a reference cervical vertebra, in particular the seventh cervical vertebra, called C7;

c) depicting, on the x-ray, a first curved segment beginning at the center of the plate of S1, tangent to the segment going from the center of S2 to the center of the plate of S1, passing through the centers of the bodies of the vertebrae of segment L5-L1 and ending at the center of the lower plate of said reference dorsal vertebra;

d) depicting, on the x-ray, a second curved segment tangent to the first curved segment at the center of the lower plate of said reference dorsal vertebra, passing through the centers of the bodies of the vertebrae of the segment extending between said reference dorsal vertebra and said reference cervical vertebra and going to the center of the lower plate of said reference cervical vertebra;

e) identifying, on that x-ray, the correction(s) to be made to the vertebral column;

f) pivoting portions of said x-ray relative to other portions of that x-ray, based on the corrections to be made, so as to show the correction(s) to be made to the vertebral column;

g) recalculating said first and second curved segments based on the correction(s) made in step f) and depicting those curved segments on said x-ray;

h) determining the length of the vertebral segment to be corrected, therefore the length of each vertebral rod to be implanted;

i) for each vertebra of that segment, either reading, on said x-ray, the distance from the center of the body of the vertebra to the posterior face of the pedicle of that vertebra, i.e., the entry face of a pedicle screw in that pedicle; or reading that same distance in a previously established databank, containing, for each vertebra, the mean value, established statistically, of that distance for the type of patient in question, in particular based on the age, gender and size of that patient;

j) performing, on said x-ray, a displacement of the sagittal curvature segment determined in step g), extending over the vertebral segment to be corrected determined in step h), over the distances read in step i) for the vertebrae in question, and recalculating the curvature of that segment in the displacement position;

k) from a straight vertebral rod, producing the curvature of that rod according to the shape of said sagittal curvature segment in said displacement position, recalculated in step j).

The method according to the invention thereby makes it possible to impart the appropriate curvature to a straight rod easily, that rod being fully suitable for the correction to be done.

Preferably, the method also comprises the following steps:

taking a frontal x-ray of the vertebral column of the patient to be treated;

on that x-ray, identifying one or more potential portions of the vertebral column that are curved in the frontal plane, and, for each of those curved portions to be straightened, defining a reference point at the vertebra on which the curved portion begins and a reference point at the vertebra on which the curved portion ends;

for each of these curved portions, measuring the length of the segment extending between the reference points identified on that curved portion;

identifying, on the aforementioned sagittal x-ray, these same reference points on these same vertebrae, and identifying the corresponding points on said sagittal curvature segment; and performing homothetic stretching of the portion of said sagittal curvature segment extending between these corresponding points, so as to give that portion a length identical to that existing between said reference points and to thereby obtain a recalculated sagittal curvature segment, taking into account the elongation of the vertebral column resulting from the correction of that column in the frontal plane.

Preferably, the identification in step e) of the correction(s) to be done includes either the identification of posterior osteotomies to be done on the plates of one or more lumbar vertebrae in order to obtain a corrected lumbar curvature, or the determination of the shape of one or more vertebral implants to be inserted into the intervertebral spaces of those vertebrae to obtain that same corrected lumbar curvature, in particular the determination of the angulation of the wedge shape those implants must have.

Preferably, the method comprises, after step j), the transfer of data relative to the rod to be produced to a service provider responsible for producing the curvature of the rod.

Thus, a practitioner, having determined the shape of the rod to be implanted using the method according to the invention, transfers the data relative to the rod to be produced to a service provider responsible for producing the curvature of the rod. Once that curvature is produced, the service provider will deliver the curved rod to the practitioner, who will be able to operate on the patient with his vertebral rod that is ready to be implanted.

The invention will be well understood, and other features and advantages thereof will appear, in reference to the appended diagrammatic drawing, showing, as a non-limiting example, different steps of the method in question.

DESCRIPTION OF THE PREFERRED EMBODIMENTS

Figure 1:
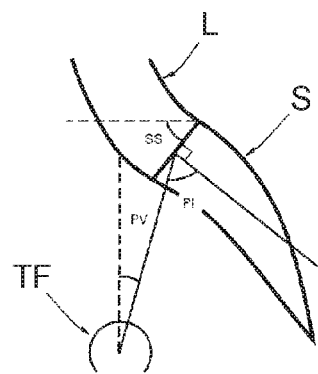
FIG. 1 is a diagrammatically view of the base of a vertebral column.
Figure 2:
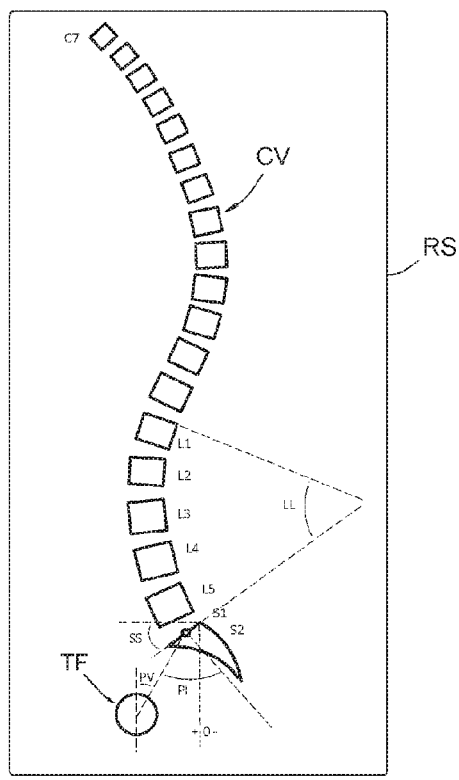
FIG. 2 is a very diagrammatic view of a vertebral column CV as shown on an x-ray, referencing the lumbar lordosis LL, the names of the vertebrae S2-L5 in question, the femoral heads TF, a point situated at the center of the plate of S1, and the pelvic criteria SS, PV, PI explained above in reference to FIG. 1.

FIGS. 2 to 11 illustrate a method making it possible to produce the ideal curvature of a vertebral rod TV that is a part of a vertebral osteosynthesis equipment, designed to correct a patient's vertebral column by performing a correction of that vertebral column. This method comprises the following successive steps:

FIG. 2: taking a sagittal preoperative x-ray RS of the vertebral column of the patient to be treated, extending from the cervical vertebrae to the femoral heads, and identifying, on that x-ray RS:

LL: the vertebral segment to be treated;

L1, L2, L3, L4, L5, S1, S2, T12, C7: the first, second, third, fourth and fifth lumbar vertebrae, the first and second vertebrae of the sacrum, the twelfth dorsal vertebra and the seventh cervical vertebra, respectively;

SS, PV, PI: the aforementioned pelvic criteria;

TF: the femoral heads, shown by a circle in the figure;

also identifying, by a dot, the center of the plate of S1.

Figure 3:
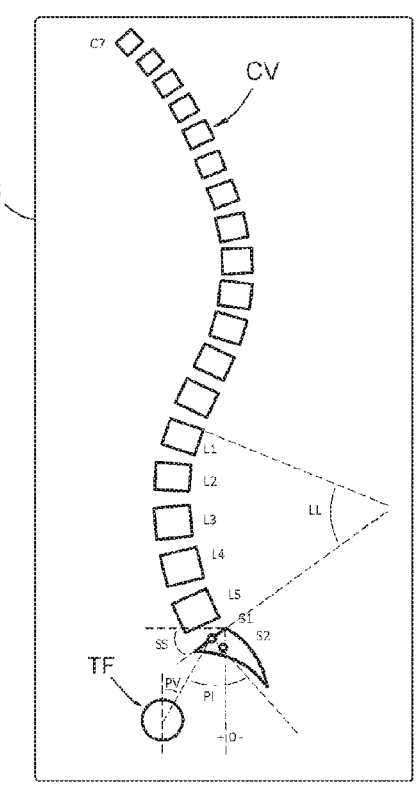
FIG. 3 is a view similar to FIG. 2, in which the center point of the second vertebra of the sacrum, called S2, is shown.

FIG. 3: identifying, on the x-ray RS, the center of the plate of S2 using a dot.

Figure 4:
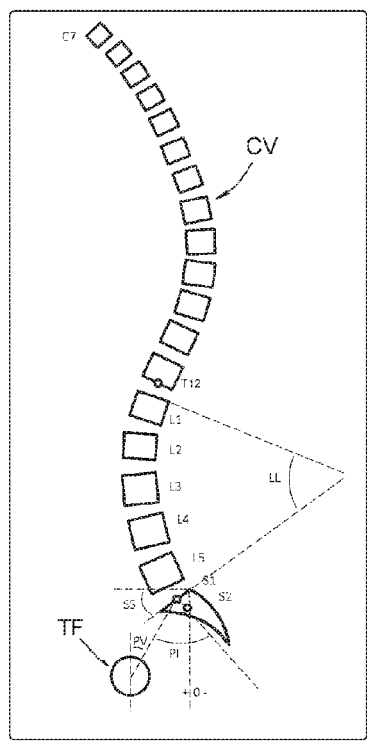
FIG. 4 is a view similar to FIG. 3, in which the center point of the lower plate of the twelfth dorsal vertebra, called T12, is shown.

FIG. 4: identifying, on the x-ray RS, the center of the lower plate of T12 using a dot.

Figure 5:
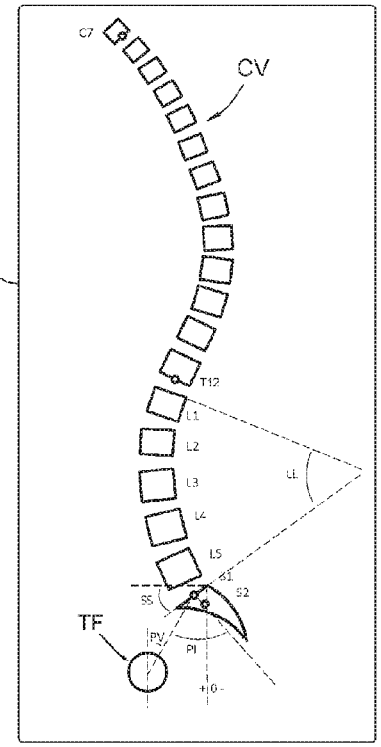
FIG. 5 is a view similar to FIG. 4, in which the center point of the lower plate of the seventh cervical vertebra, called C7, is shown.

FIG. 5: identifying, on the x-ray RS, the center of the lower plate of C7 using a dot.

Figure 6:
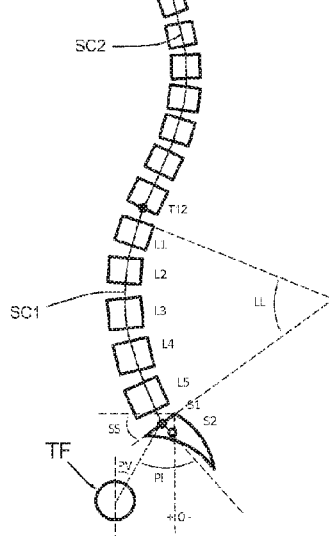
FIG. 6 is a view similar to FIG. 5, in which a first curved segment SC1 and a second curved segment SC2 are further shown.

FIG. 6: depicting, on said x-ray RS, said first and second curved segments SC1, SC2; the first curved segment SC1 begins at the center of the plate of S1, tangent to the segment going from the center of S2 to the center of the plate of S1, passes through the centers of the bodies of the vertebrae of segment L5-L1 and ends at the center of the lower plate of T12; the second curved segment SC2 is tangent to the first curved segment SC1 at the center of the lower plate of T12, passes through the centers of the bodies of the vertebrae of segment T11-C6 and goes to the center of the lower plate of C7.

Figure 7:
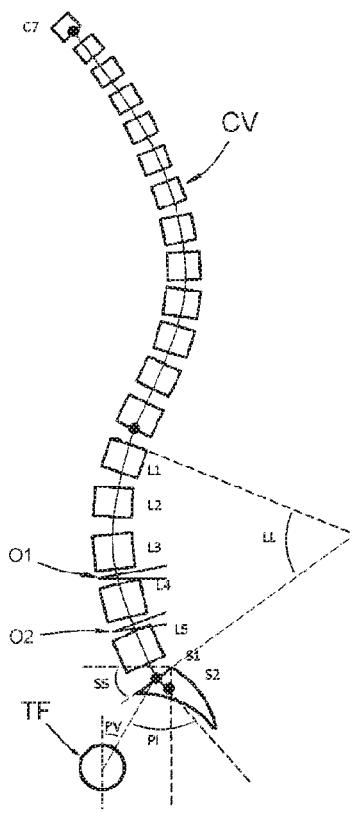
FIG. 7 is a view similar to FIG. 6, in which osteotomies O1, O2 to be done on the upper plates, posterior sides, of vertebrae L4 and L5 (fourth and fifth lumbar vertebra) are also shown.

FIG. 7: identifying, on the x-ray RS, the correction(s) of the vertebral column that must be performed, and in particular identifying the osteotomies O1, O2 to be done in order to obtain a corrected lumbar curvature; in the illustrated example, the determination is made to perform an osteotomy O1 of 10.degree. on the upper plate of L4 and an osteotomy O2 of 10.degree. on the upper plate of L5.

Figure 8:
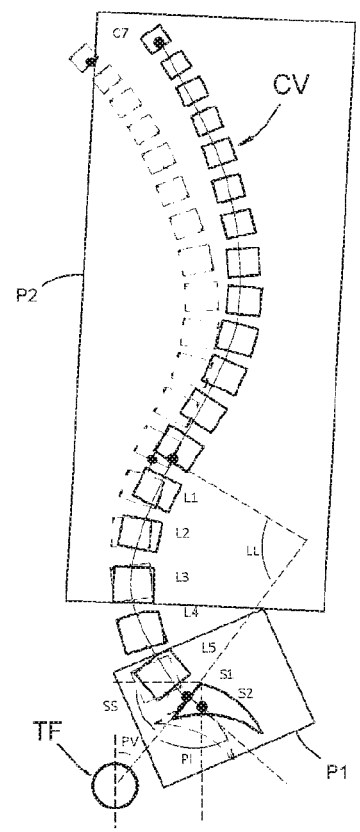
FIG. 8 is a view similar to FIG. 7, showing two portions P1, P2 of the x-ray, delimited by frames, that have been pivoted relative to the respective positions that those same portions occupy in FIG. 7, in the counterclockwise direction regarding P1 and the clockwise direction regarding P2; these new positions are corrected positions of the vertebral column CV, made possible by the corrected lumbar curvature made possible by the osteotomies O1, O2 to be done; in order to view the correction made, the uncorrected vertebral column, as shown in FIG. 7, is superimposed on the corrected vertebral column shown by FIG. 8, that uncorrected vertebral column being shown in thin and broken lines.

FIG. 8: pivoting the portions P1 and P2 of the x-ray RS relative to the rest of that x-ray RS, based on the osteotomies O1, O2 to be done; in the illustrated example, the portion P1 pivots by 10.degree. in the counterclockwise direction relative to the portion of the x-ray on which L4 is located (angulation made possible by the osteotomy O2) and the portion P2 pivots by 10.degree. in the clockwise direction relative to the portion of the x-ray on which L4 is located (angulation made possible by the osteotomy O1). Said first and second curved segments SC1 and SC2 are then recalculated based on the correction(s) made and are shown on the x-ray RS.

Figure 9:
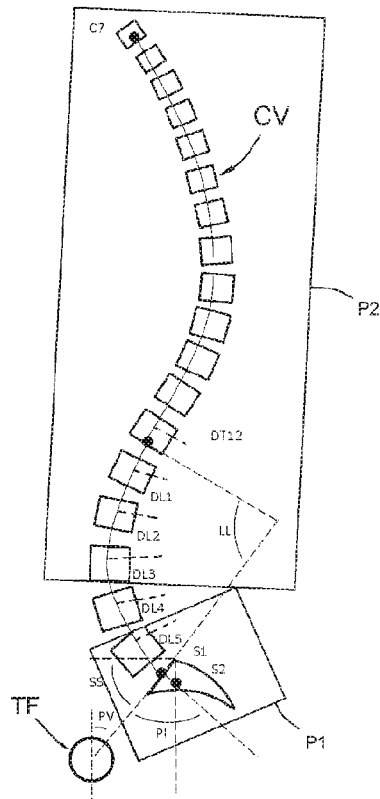
FIG. 9 is a view similar to FIG. 8, showing, in broken lines, the respective distances DL5 to DT12 which, for each of vertebrae L5 to T12, go from the center of the body of the vertebra to the posterior face of a pedicle of that vertebra.
Figure 10:
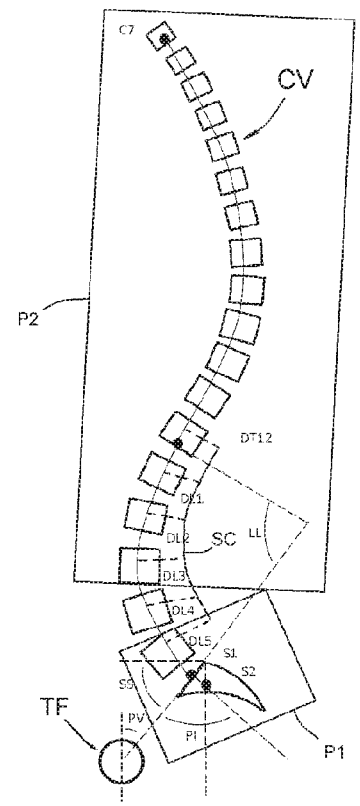
FIG. 10 is a view similar to FIG. 9, showing a sagittal curvature segment SC that corresponds to the curvature to be given to a vertebral rod to produce the desired correction of the vertebral column.

FIG. 9: the length of the vertebral segment to be corrected is determined (in the case at hand, L5-T12), which makes it possible to determine the length of each vertebral rod TV to be implanted; for each vertebra of that segment, the respective distances DL5 to DT12 are determined from the center of the body of the vertebrae to the posterior face of a pedicle of that vertebra, i.e., the entry face of a pedicle screw in the pedicle; these distances are either read on the x-ray RS, or are read in a previously established databank, containing, for each vertebra, the mean value, established statistically, of that distance for the type of patient in question, in particular based on the age, gender and size of that patient;

FIG. 10: a displacement of the curved segment is then done, on the x-ray RS, over the respective distances DL5 to DT12, and the curvature of that segment is recalculated in the displacement position.

Figure 11:
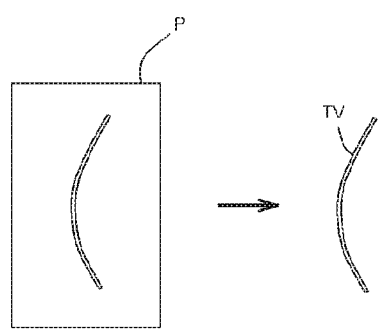
FIG. 11 is, on the left side of that figure, a view of a plane of the curved vertebral rod to be obtained, established from said sagittal curvature segment SC, and, on the right side of that figure, a view of the curved vertebral rod TV, obtained from that plane P.

FIG. 11: after the diameter of the vertebral rod TV to be used has been determined based on the patient in question, a plane P of the curvature of that rod is established, from which the rod TV is made, by curvature from a straight vertebral rod, in particular by cold bending.

Figures 12, 13:
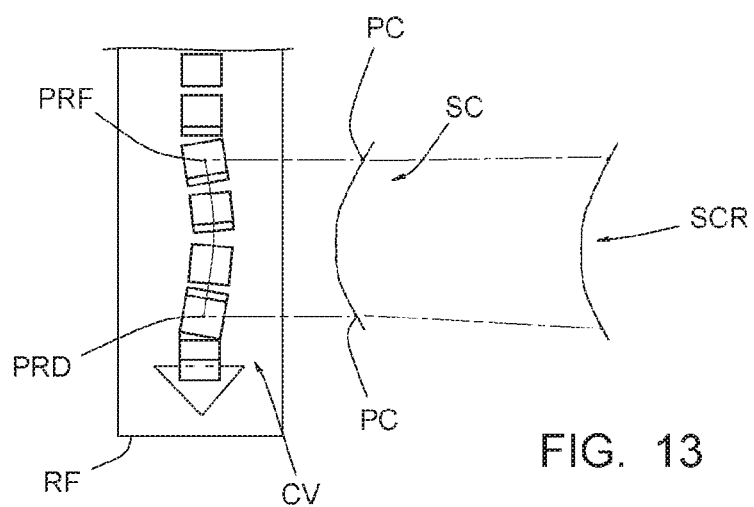
FIG. 12 is, on the left, a partial view of a frontal x-ray RF of the vertebral column of the patient to be treated, and, on the right, a side view of said sagittal curvature segment SC, on which reference points PC are identified.
FIG. 13 is a view of a recalculated sagittal curvature segment SCR, obtained following stretching of a portion of the sagittal curvature segment SC.

FIGS. 12 and 13 show the following steps that the method may comprise:

FIG. 12:

also taking a frontal x-ray RF of the vertebral column CV of the patient to be treated;

on that x-ray RF, identifying one or more potential portions of that vertebral column CV that are curved in the frontal plane, and which must therefore be corrected, and a reference point PRD at the center of the body of the vertebra on which the curved portion begins and a reference point PRF at the center of the body of the vertebra on which the curved portion ends;

measuring the length of the curved segment extending between those reference points PRD, PRF;

identifying, on the aforementioned sagittal x-ray RS, these same reference points PRD, PRF on these same vertebrae, and identifying the corresponding points PC on said sagittal curvature segment SC; and performing homothetic stretching of the portion of said sagittal curvature segment SC extending between these corresponding points PC, so as to give that portion a length identical to that separating the aforementioned reference points PRD, PRF.

FIG. 13: a recalculated sagittal curvature segment SCR is thus obtained, taking the elongation of the vertebral column resulting from the correction of that column in the frontal plane into account.

The method according to the invention thus has the decisive advantage of making it possible to produce the ideal curvature of a rod for vertebral osteosynthesis equipment designed to correct a patient's vertebral column.

What is claimed is:

1. A system for manufacturing a curvature of a rod for vertebral osteosynthesis equipment designed to correct a vertebral column of a patient, the system comprising:
    an interface for analyzing a sagittal preoperative x-ray of the vertebral column extending from cervical vertebrae to femoral heads, wherein the sagittal preoperative x-ray is analyzed by:
    identifying on the x-ray:
    a center of a plate of a first vertebra of a sacrum;
    a center of a plate of a second vertebra of the sacrum;
    a center of a lower plate of a reference dorsal vertebra; and
    a center of a lower plate of a reference cervical vertebra;
    depicting a first curved segment, the first curved segment beginning at the center of the plate of the first vertebra, wherein the first curved segment is tangent to a straight segment from the center of the second vertebra to the center of the first vertebra and passes through centers of bodies of vertebrae of segments L5-L1 and ending at the center of the lower plate of the reference dorsal vertebra;
    depicting a second curved segment, wherein the second curved segment is tangent to the first curved segment at the center of the lower plate of the reference dorsal vertebra and passes through centers of bodies of vertebrae of segments T11-C6 and going to the center of the lower plate of the reference cervical vertebra;

identifying one or more corrections to be made to the vertebral column;

pivoting a first portion relative to a portion of the x-ray comprising L4 and pivoting a second portion relative to the portion of the x-ray comprising L4 to determine one or more corrections to be made to the vertebral column;

recalculating the first curved segment and the second curved segment based on the determined one or more corrections and depicting the first curved segment and the second curved segment on the x-ray;

calculating a length of a rod to be implanted based on determining a length of a vertebral segment to be corrected, wherein the length of the vertebral segment to be corrected is calculated by:

for each vertebra of the vertebral segment to be corrected, calculating a distance from a center of a body of the vertebra to an entry face of a pedicle screw in a pedicle of the vertebra; or obtaining the distance from a database containing, for each vertebra, a mean value, established statistically of the distance for a type of patient based on age, gender, and size;

displacing the recalculated first and second curved segments extending over the vertebral segment to be corrected and determining a curvature of the vertebral segment to be corrected in the displaced position;

the interface further configured to determine a diameter of the rod based on the analyzed x-ray;

the interface further configured to determine a curvature of the rod based on the analyzed x-ray; and the interface further configured to generate data instructions based on the determined diameter and the determined curvature of the rod, the generated data instructions configured for use by a manufacturing apparatus configured to manufacture the rod, wherein the interface comprises a computer processor and an electronic storage medium.

2. The system of claim 1, wherein the interface is further configured to analyze a frontal preoperative x-ray of the vertebral column of the patient, wherein the frontal preoperative x-ray is analyzed by:

identifying one or more portions of the vertebral column that is curved in a frontal plane;

for each of the one or more portions, defining a first reference point in the vertebra at which a curvature begins and a second reference point in the vertebra at which the curvature ends;

for each of the one or more portions, determining a length extending between the first reference point and the second reference point; and identifying, on the sagittal preoperative x-ray, the first reference point and the second reference point for each of the one or more portions, and identifying a first corresponding point and a second corresponding point.

3. The system of claim 2, wherein the frontal preoperative x-ray is further analyzed by:

performing homothetic stretching of first and second curved segments in the sagittal x-ray extending between the first corresponding point and the second corresponding point to obtain a length that corresponds to a length between the first reference point and the second reference point; and recalculating the first and second curved segments, taking into account elongation of the vertebral column resulting from correction of the vertebral column in a frontal plane.

4. The system of claim 1, wherein identifying one or more corrections to be made to the vertebral column comprises identifying one or more posterior osteotomies to be performed on one or more plates of a lumbar vertebrae to obtain a corrected lumbar curvature.

5. The system of claim 1, wherein identifying one or more corrections to be made to the vertebral column comprises determining a shape of one or more vertebral implants to be inserted into one or more intervertebral spaces of a lumbar vertebrae to obtain a corrected lumbar curvature.

6. The system of claim 5, wherein the determined shape of the one or more vertebral implants comprises an angulation of a wedge shape of the one or more vertebral implants.

7. The system of claim 3, wherein identifying one or more corrections to be made to the vertebral column comprises identifying one or more posterior osteotomies to be performed on one or more plates of a lumbar vertebrae to obtain a corrected lumbar curvature.

8. The system of claim 3, wherein identifying one or more corrections to be made to the vertebral column comprises determining a shape of one or more vertebral implants to be inserted into one or more intervertebral spaces of a lumbar vertebrae to obtain a corrected lumbar curvature.

9. The system of claim 8, wherein the determined shape of the one or more vertebral implants comprises an angulation of a wedge shape of the one or more vertebral implants.

10. The system of claim 1, wherein the interface is further configured to transmit the generated data instructions to a service provider for producing a curvature of the rod.

11. The system of claim 1, wherein the reference dorsal vertebra is a twelfth dorsal vertebra.

12. The system of claim 1, wherein the reference cervical vertebra is a seventh cervical vertebra.

13. The system of claim 1, wherein the one or more corrections to be made to the vertebral column are identified by performing one or more osteotomies.

14. The system of claim 1, wherein the one or more osteotomies are performed on one or more of an upper plate of L4 and an upper plate of L5.

15. The system of claim 1, wherein the rod is configured to be manufactured by cold bending.

* * * * *